(12) United States Patent
Dewey et al.

(10) Patent No.: US 8,123,808 B2
(45) Date of Patent: Feb. 28, 2012

(54) VERTEBRAL ENDPLATE CONNECTION IMPLANT AND METHOD

(75) Inventors: Jonathan M. Dewey, Sunnyvale, CA (US); Marcel F. Dvorak, Vancouver (CA); Charles G. Fisher, Vancouver (CA); Anthony J. Melkent, Memphis, TN (US); Keith E. Miller, Germantown, TN (US); Y. Raja Rampersaud, Toronto (CA)

(73) Assignee: Warsaw Orthopedic, Inc., Warsaw, IN (US)

( * ) Notice: Subject to any disclaimer, the term of this patent is extended or adjusted under 35 U.S.C. 154(b) by 296 days.

(21) Appl. No.: 12/424,663

(22) Filed: Apr. 16, 2009

(65) Prior Publication Data

US 2010/0268343 A1 Oct. 21, 2010

(51) Int. Cl.
*A61F 2/44* (2006.01)
(52) U.S. Cl. .................................................... 623/17.12
(58) Field of Classification Search ..... 623/17.11–17.16
See application file for complete search history.

(56) References Cited

U.S. PATENT DOCUMENTS

| | | | |
|---|---|---|---|
| 3,875,595 A | 4/1975 | Froning | |
| 4,335,713 A * | 6/1982 | Komiya | 600/114 |
| 4,553,273 A | 11/1985 | Wu | |
| 4,554,914 A * | 11/1985 | Kapp et al. | 606/86 A |
| 4,599,086 A | 7/1986 | Doty | |
| 4,636,217 A | 1/1987 | Ogilvie et al. | |
| 4,892,545 A * | 1/1990 | Day et al. | 623/17.11 |
| 4,932,975 A | 6/1990 | Main et al. | |
| 5,015,255 A | 5/1991 | Kuslich | |
| 5,071,437 A * | 12/1991 | Steffee | 623/17.16 |
| 5,236,460 A | 8/1993 | Barber | |
| 5,290,312 A | 3/1994 | Kojimoto et al. | |
| 5,336,223 A | 8/1994 | Rogers | |
| 5,571,189 A | 11/1996 | Kuslich | |
| 5,571,190 A | 11/1996 | Ulrich et al. | |
| 5,683,465 A * | 11/1997 | Shinn et al. | 623/17.14 |
| 5,827,328 A | 10/1998 | Buttermann | |
| 6,299,644 B1 | 10/2001 | Vanderschot | |
| 6,375,682 B1 | 4/2002 | Fleischmann et al. | |
| 6,805,697 B1 | 10/2004 | Helm et al. | |
| 7,220,282 B2 | 5/2007 | Kuslich | |
| 7,226,481 B2 | 6/2007 | Kuslich | |
| 7,309,338 B2 | 12/2007 | Cragg | |
| 7,645,301 B2 * | 1/2010 | Hudgins et al. | 623/17.12 |
| 7,674,296 B2 * | 3/2010 | Rhoda et al. | 623/17.15 |

(Continued)

FOREIGN PATENT DOCUMENTS

DE 4109941 A1 10/1992

(Continued)

OTHER PUBLICATIONS

Steinmetz, Management of Metastatic Tumors of the Spine: Strategies and Operative Indications, Neurosurg Focus 11(6), 2001, © 2001 American Association of Neurological Surgeons, pp. 1-9.

(Continued)

*Primary Examiner* — Eduardo C Robert
*Assistant Examiner* — Jacqueline Johanas (57) ABSTRACT

Embodiments of the invention include implants and methods for connecting devices to bones, such as one or more endplates of vertebrae. Devices may include mechanisms for connecting to one or more vertebrae by extending portions of the devices through an aperture in a vertebral implant and expanding the implant within the one or more vertebrae. A fill material may be used to drive the expansion in some embodiments.

7 Claims, 8 Drawing Sheets

U.S. PATENT DOCUMENTS

| | | | |
|---|---|---|---|
| 2003/0083749 A1 | 5/2003 | Kuslich et al. | |
| 2003/0220649 A1 | 11/2003 | Bao et al. | |
| 2005/0027362 A1 | 2/2005 | Williams et al. | |
| 2005/0154460 A1* | 7/2005 | Yundt | 623/17.11 |
| 2005/0261695 A1* | 11/2005 | Cragg et al. | 606/86 |
| 2006/0235535 A1 | 10/2006 | Ferree et al. | |
| 2006/0293750 A1 | 12/2006 | Sherman et al. | |
| 2007/0168031 A1* | 7/2007 | Hudgins et al. | 623/17.12 |
| 2007/0173940 A1 | 7/2007 | Hestad et al. | |
| 2008/0021556 A1* | 1/2008 | Edie | 623/17.11 |
| 2008/0058931 A1* | 3/2008 | White et al. | 623/17.11 |
| 2008/0167726 A1 | 7/2008 | Melkent | |
| 2009/0187248 A1* | 7/2009 | Dewey et al. | 623/17.16 |
| 2009/0270987 A1* | 10/2009 | Heinz et al. | 623/17.16 |
| 2010/0063510 A1* | 3/2010 | Arlet et al. | 606/93 |
| 2010/0087924 A1* | 4/2010 | Arlet | 623/17.12 |
| 2010/0114319 A1* | 5/2010 | Edie | 623/17.12 |
| 2010/0204794 A1* | 8/2010 | Jarzem et al. | 623/17.12 |
| 2010/0292794 A1* | 11/2010 | Metz-Stavenhagen | 623/17.11 |
| 2011/0004307 A1* | 1/2011 | Ahn et al. | 623/17.12 |

FOREIGN PATENT DOCUMENTS

| | | |
|---|---|---|
| DE | 20017962 U1 | 1/2001 |
| EP | 1212992 B1 | 8/2007 |
| WO | 0103614 A1 | 1/2001 |
| WO | 2004016217 A2 | 2/2004 |
| WO | 2005071190 A2 | 8/2005 |
| WO | 2007124253 A2 | 11/2007 |
| WO | 2008144175 A1 | 11/2008 |

OTHER PUBLICATIONS

Errico, A New Method of Thoracic and Lumbar Body Replacement for Spinal Tumors: Technical Note, ISSN: 0148-396X, Accession: 00006123-199304000-00030, vol. 32(4), Apr. 1993, p. 678-681, Copyright © by the Congress of Neurological Surgeons, Departments of Orthopedics and Neurosurgery, New York University Medical Center, New York, NY.

* cited by examiner

VERTEBRAL ENDPLATE CONNECTION IMPLANT AND METHOD

FIELD OF THE INVENTION

The present invention relates generally to the field of replacing portions of the human structural anatomy with medical implants, and in some embodiments more particularly relates to an implant and method for connecting to one or more endplates of vertebrae.

BACKGROUND

Connecting to the endplates of vertebral bodies is useful in at least some spinal fusion procedures and in at least some vertebral body replacement procedures. Spinal fusion procedures are often effective to restore proper vertebral spacing and relieve pressure on nerves and consequent pain. Also, it is sometimes necessary to remove one or more vertebrae, or a portion of the vertebrae, from the human spine in response to various pathologies. For example, one or more of the vertebrae may become damaged as a result of tumor growth, or may become damaged by a traumatic or other event. Removal, or excision, of a vertebra may be referred to as a vertebrectomy. Excision of a generally anterior portion, or vertebral body, of the vertebra may be referred to as a corpectomy. An implant is usually placed between the remaining vertebrae to provide structural support for the spine as a part of a corpectomy or vertebrectomy. This may generally be referred to as vertebral body replacement.

Endplate connections have been accomplished traditionally in the art with the aid of screws, spikes, teeth, keels, penetrations into the endplates, and various other fasteners and techniques. However, the prior art has been limited in supplying a solution that provides significant fixation across the interface between an implant and a vertebral endplate that may be delivered with minimal disruption to the surrounding tissues and with minimal surgical manipulation of the vertebral endplate. Further, in some circumstances, it would be advantageous to add stabilizing material inside vertebrae to which an implant is being connected and to provide mechanisms for stabilizing or adhesive materials to interact with the vertebrae.

Connections between bones and implants may also be useful in replacing bones or portions of joints or appendages such as the legs and arms, or other bones. Examples include, but are not limited to, a femur, tibia, fibula, humerus, radius, ulna, phalanges, clavicle, and any of the ribs. Use of the mechanisms described and claimed herein are equally applicable to treatment or repair of such bones or appendages.

SUMMARY

An embodiment of the invention is an implant for placement adjacent to at least one vertebral endplate. The implant may include an intervertebral structure and a nozzle extending away from the intervertebral structure configured to penetrate the at least one vertebral endplate. The nozzle of some embodiments includes one or more sides that extend away from the intervertebral structure, and an opening near a distal end of the one or more sides. The opening is configured to open through the at least one vertebral endplate and into the vertebra. Embodiments include a port in the intervertebral structure that is in fluid communication with the nozzle. The port is for receiving a fill material.

Another embodiment of the invention is an implant for placement adjacent to at least one vertebral endplate. The embodiment may include an intervertebral structure including a bag that is next to the at least one vertebral endplate in an unexpanded state and is configured to at least in part penetrate the vertebral endplate through an aperture in the vertebral endplate in an expanded state. The bag is configured in some embodiments to expand to a greater lateral dimension inside a vertebra than the lateral dimension of the aperture. The implant may also include a membrane configured to expand laterally in a space between vertebrae when in an expanded state. The bag and the membrane may be in fluid communication with a fill material source.

Still another embodiment of the invention is a method of stabilizing a spine. The method may include forming an aperture in a vertebral endplate, placing an implant with a bag in an unexpanded state adjacent to the vertebral endplate aperture, and introducing a fill material into the bag to expand the bag through the vertebral endplate aperture and into a vertebra. The act of introducing the fill material may also laterally expand the bag to a lateral dimension that is greater than a lateral dimension of the aperture in the vertebral endplate.

DETAILED DESCRIPTION

Figure 1:
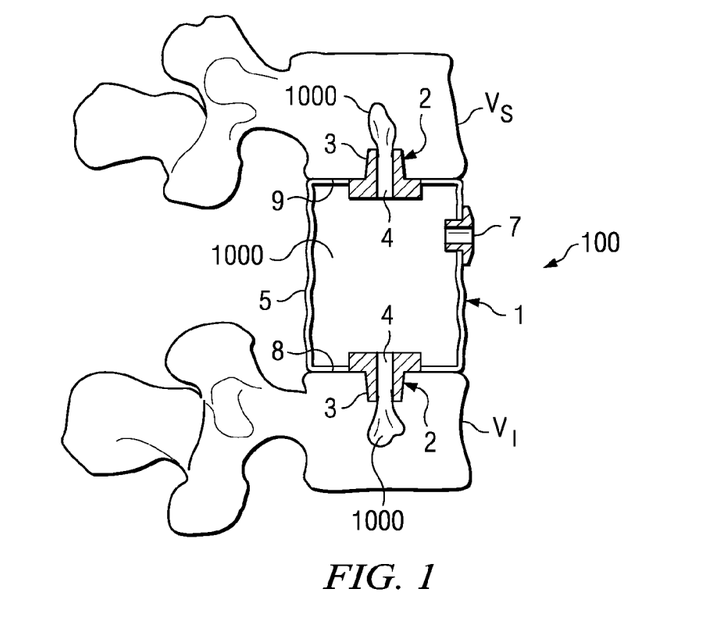
FIG. 1 is a cross-sectional view of an embodiment of an implant between vertebral bodies.

FIG. 1 shows an implant 100 between a superior vertebra $V_S$ and an inferior vertebra $V_I$. The implant 100 shown is adjacent a superior vertebral endplate 9 and an inferior vertebral endplate 8. The implant 100 includes an intervertebral structure 1 and two nozzles 2. A port 7 in the intervertebral structure 1 is shown in fluid communication with the nozzles 2 through the intervertebral structure 1, and specifically through a membrane 5 that couples with the nozzles 2 and the port 7. The port 7 may be used to receive a fill material 1000 into the implant 100.

The illustrated intervertebral structure 1 is a vertebral body replacement device. However, in other embodiments the intervertebral structure 1 may be a spinal disc replacement device. A spinal disc replacement device may replace all or merely a part of a spinal disc. The spinal disc replacement device may be rigid or flexible. It may function as a dynamic device, or it may serve as a spacing device for a fusion procedure. In some embodiments, the intervertebral structure 1 may be a replacement for multiple spinal discs and vertebral bodies. Non-limiting examples of an intervertebral structure are shown in FIGS. 1-3, 7, 9-13, 16, and 17. FIGS. 1, 3, and 9-11 illustrate, at least in part, membranes configured to receive fill material in order to be stabilized in an expanded state. FIGS. 2, 7, and 11-13 show intervertebral structures that are constructed, at least in part, of telescoping components. Any other intervertebral structure that effectively fills a space between vertebrae, whether of a fixed height or expandable, is contemplated under embodiments of the invention.

Various embodiments of nozzles 2, 22, 32, 42, 52, 62, 72, 92, 102, 162, and 172, are illustrated in FIGS. 1-10, 16, and 17 respectively. For example, the nozzles 2 illustrated in FIG. 1 extend away from the intervertebral structure 1 and are configured to penetrate the superior vertebral implant 9 on the superior end, and the inferior vertebral implant 8 on the inferior end. In some embodiments, a nozzle may be a relatively thin member such as a jam-sheedy needle or other more narrow member than the nozzles specifically depicted herein. The nozzle 2 includes a side 3 that extends away from the intervertebral structure 1. One or more sides 3 of some embodiments have an opening 4 near their distal ends, and the opening 4 may be configured to open through a vertebral endplate 8, 9, as illustrated in FIG. 1.

The one or more sides 3, 23, 33, 43, 53, 63, 73, 93, 103, 163, and 173, may be a continuous side that forms a round cross-section or may be any number of sides that form a symmetrical or unsymmetrical polygonal cross-sectional shape. The one or more sides of some embodiments may also form only a portion of a cross-sectional shape, that is, may not form a continuous cross-section along their entire length.

Figure 2:
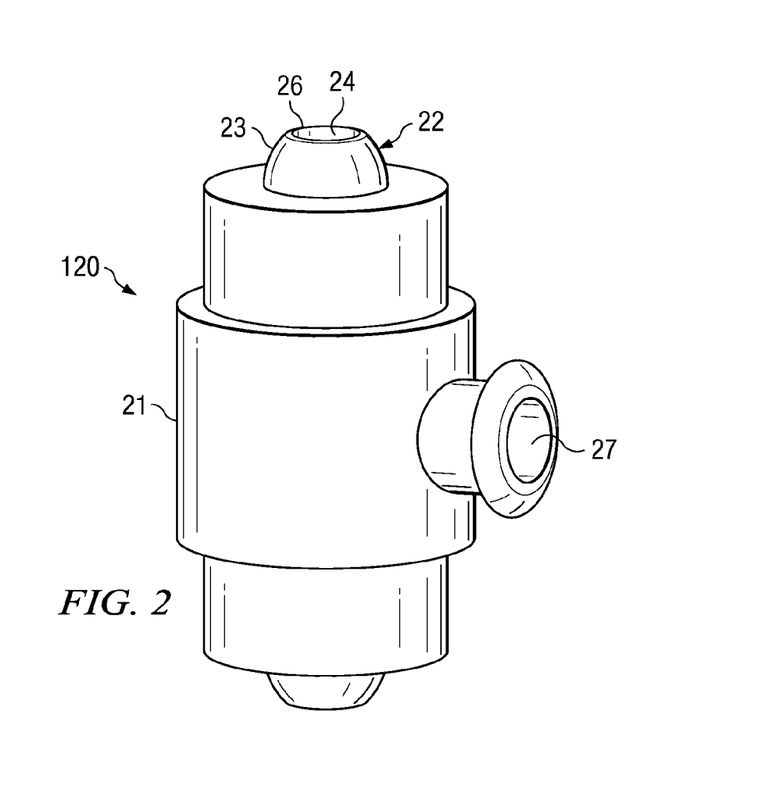
FIG. 2 is a perspective view of a portion of an embodiment of an implant.

FIG. 2 depicts an implant 120 for placement adjacent at least one vertebral endplate. An intervertebral structure 21 is shown along with a nozzle 22 having sides 23 that extend away for the intervertebral structure 21. The intervertebral structure 21 shown is a telescoping body sized to replace at least a portion of a vertebral body. The illustrated sides 23 form a round cross-section, and in addition have convex outer walls. The nozzle 22 has a generally wider structure at its proximal end where it couples with the intervertebral structure 21 and a more narrow structure at its distal end 26. This shape may be useful to assist with insertion into a vertebral endplate in some embodiments, and may assist with penetration of the vertebral endplate. The nozzle 22 has an opening 24 near the distal end 26 of the sides 23. The opening 24 is configured to open through at least one vertebral endplate in some embodiments. The nozzle 22 may be sharpened or tapered overall to assist with insertion or penetration of the vertebral endplate, and it may have a sharpened distal end 26, as shown in FIG. 2, to assist with insertion or penetration of the vertebral endplate. FIG. 2 further illustrates a port 27 in the intervertebral structure 21 that is in fluid communication with the nozzle 22. In some embodiments, the port 27 is configured to receive fill material 1000.

Figure 3:
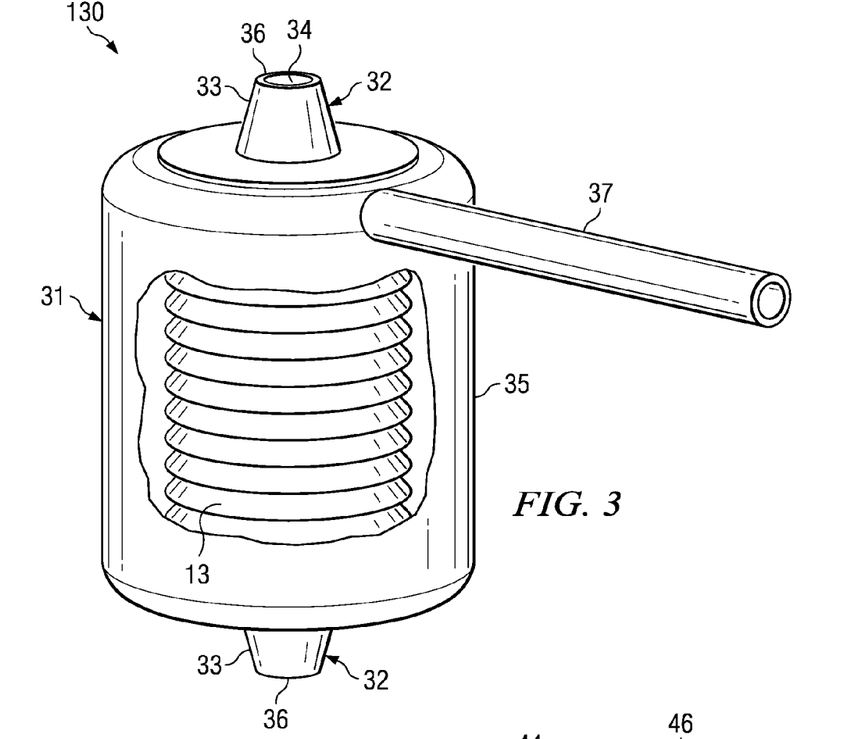
FIG. 3 is a perspective view of an embodiment of an implant.

FIG. 3 shows an implant 130 for placement adjacent at least one vertebral endplate. An intervertebral structure 31 is shown along with nozzles 32 having sides 33 that extend away for the intervertebral structure 31. The intervertebral structure 31 shown is an expandable body in a contracted or unexpanded state. A membrane 35 defining a volume and a linearly expandable component 13 coupled to the membrane and substantially contained within the volume of the membrane 35 are shown. The linearly expandable component 13 shown is an expandable bellows mechanism. The linearly expandable component 13 may also be laterally rigid in some embodiments. The linearly expandable component 13 illustrated is configured to receive a fluid that drives linear expansion of the intervertebral structure 31 or maintains linear expansion of the intervertebral structure 31. In the illustrated embodiment, a fluid may be introduced through a port 37. The fluid may be merely for expansion and retention, or may be a component of the fill material 1000. In some embodiments, the port 37 is configured to receive fill material 1000. A fluid may be a paste, gel, liquid, suspension, granular mixture, or similar substance. A substance as described herein will be considered a fluid even if it later cures or hardens to a non-fluidic state. Both the linearly expandable component 13 and the membrane 35 are unexpanded linearly in the illustration. The port 37 may be used to handle the intervertebral structure 31 or to guide the implant into a position where it can be effectively deployed. The port 37 in the intervertebral structure 31 is in fluid communication with the nozzles 32. The illustrated nozzles 32 are open to the interior of the linearly expandable component 13. The sides 33 shown in FIG. 3 form a round cross-section, and taper to form frusto-conical nozzles 32. Each nozzle 32 has a generally wider structure at its proximal end where it couples with the intervertebral structure 31 and a more narrow structure at its distal end 36. This shape may be useful to assist with insertion into a vertebral endplate in some embodiments, and may assist with penetration of the vertebral endplate. The nozzle 32 has an opening 34 near the distal end 36 of the sides 33. The opening 34 is configured to open through at least one vertebral endplate in some embodiments. The nozzle 32 may be sharpened or tapered overall to assist with insertion or penetration of the vertebral endplate, and it may have a sharpened distal end 36 to assist with insertion or penetration of the vertebral endplate.

Figure 4:
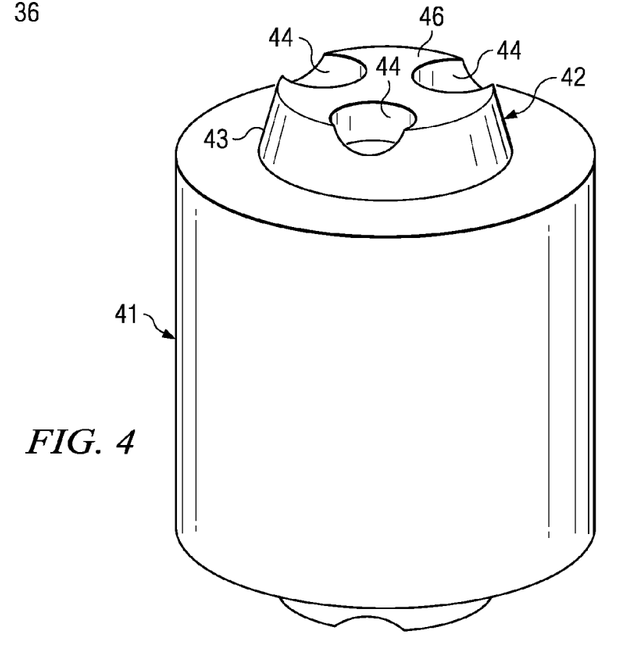
FIG. 4 is a perspective view of an end of an implant embodiment.
Figures 5, 6, 7, 8:
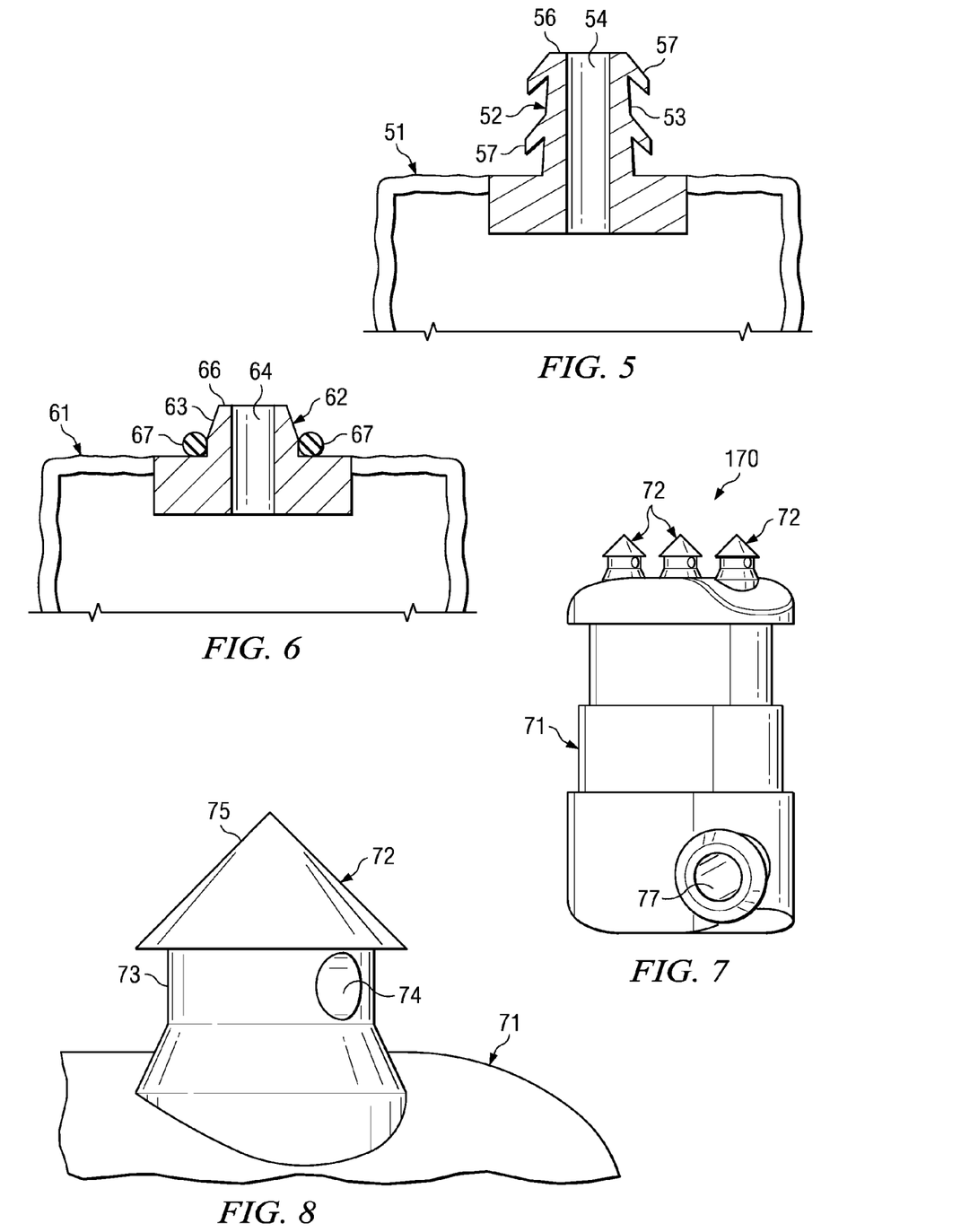
FIG. 5 is a cross-sectional view of an end of an implant embodiment.
FIG. 6 is a cross-sectional view of an end of an implant embodiment.
FIG. 7 is a perspective view of a portion of an embodiment of an implant.
FIG. 8 is a perspective view of a nozzle of the implant of FIG. 7.

FIGS. 4-6 illustrate embodiments of the nozzles 42, 52, and 62. Each of the illustrated nozzles may be used with any disclosed or otherwise functional intervertebral structure 41, 51, 61, such as, but without limitation, a membrane, a telescoping body, or a bellows mechanism. The nozzle 42 of FIG. 4 has sides 43 that extend away for the intervertebral structure 41. The illustrated sides 43 form a round cross-section, and taper to form a frusto-conical nozzle 42. The nozzle 42 has a generally wider structure at its proximal end where it couples with the intervertebral structure 41 and a more narrow structure at its distal end 46. This shape may be useful to assist with insertion into a vertebral endplate in some embodiments, and may assist with penetration of the vertebral endplate. The nozzle 42 has three openings 44 near the distal end 46 of the sides 43. The openings 44 are configured to open through at least one vertebral endplate in some embodiments. Providing multiple openings 44 may permit increased area for fluid flow while adding structural strength to the nozzle 42 in some embodiments. The nozzle 42 may be sharpened or tapered overall to assist with insertion or penetration of the vertebral endplate, and it may have a sharpened distal end 46 to assist with insertion or penetration of the vertebral endplate. Embodiments may also include a port in the intervertebral structure 41 that is in fluid communication with the nozzle 42. In some embodiments, the port is configured to receive fill material 1000.

The nozzle 52 of FIG. 5 has sides 53 that extend away for the intervertebral structure 51. The illustrated sides 53 form a round cross-section. The illustrated nozzle 52 includes projections 57 extending from at least one of the sides 53. The projections 57 depicted are configured to resist migration of the nozzle 52 away from a vertebral endplate in which the nozzle has been inserted. The projections may, without limitation, be individual components such as teeth, barbs, ridges, or spikes. The projections of some embodiments may also be continuous or nearly continuous rings, washers, or other devices around the periphery of the nozzle 52. The nozzle 52 has an opening 54 near a distal end 56 of the sides 53. The opening 54 is configured to open through at least one vertebral endplate in some embodiments. The nozzle 52 may be sharpened or tapered overall to assist with insertion or penetration of the vertebral endplate, and it may have a sharpened distal end 56 to assist with insertion or penetration of the vertebral endplate. Embodiments may also include a port in the intervertebral structure 51 that is in fluid communication with the nozzle 52. In some embodiments, the port is configured to receive fill material 1000.

The nozzle 62 of FIG. 6 has sides 63 that extend away for the intervertebral structure 61. The illustrated sides 63 form a round cross-section. A seal 67 is illustrated adjacent to the nozzle 62 in a position to fit between the nozzle 62 and a vertebral endplate. The seal 67 may include, without limitation, a ring, gasket, washer, filling, putty, or other structure that partially or completely restricts flow of fill material between the nozzle 62 and a vertebral endplate. The seal 67 may function as a soft material that conforms to the shape of the nozzle 62 and vertebral endplate, or may restrict flow by being recessed in or penetrating one or both of the nozzle 62 and the vertebral endplate. The nozzle 62 has an opening 64 near a distal end 66 of the sides 63. The opening 64 is configured to open through at least one vertebral endplate in some embodiments. The nozzle 62 may be sharpened or tapered overall to assist with insertion or penetration of the vertebral endplate, and it may have a sharpened distal end 66 to assist with insertion or penetration of the vertebral endplate. Embodiments may also include a port in the intervertebral structure 61 that is in fluid communication with the nozzle 62. In some embodiments, the port is configured to receive fill material 1000.

FIGS. 7 and 8 in combination show an implant 170 for placement adjacent at least one vertebral endplate. An intervertebral structure 71 is shown along with three nozzles 72 having sides 73 that extend away for the intervertebral structure 71. The intervertebral structure 71 shown is a telescoping body sized to replace at least a portion of a vertebral body. The illustrated sides 73 form a round cross-section. The nozzle 72 more specifically illustrated in FIG. 8 is coupled to the intervertebral structure 71 at its proximal end. The nozzle 72 shown also includes a cap 75 over the distal end of the nozzle 72 and an opening 74 in the side 73 of the nozzle 72 near the distal end. In some embodiments, and as illustrated in FIG. 8, the cap 75 has a sharpened distal end 76. The sharpened distal end 76 may be useful to assist with insertion into a vertebral endplate in some embodiments, and may assist with penetration of the vertebral endplate. The opening 74 is configured to open through at least one vertebral endplate in some embodiments. The nozzles 72 may be tapered overall to assist with insertion or penetration of the vertebral endplate. FIG. 7 further illustrates a port 77 in the intervertebral structure 71 that is in fluid communication with the nozzles 72. In some embodiments, the port 77 is configured to receive fill material 1000.

Figure 9:
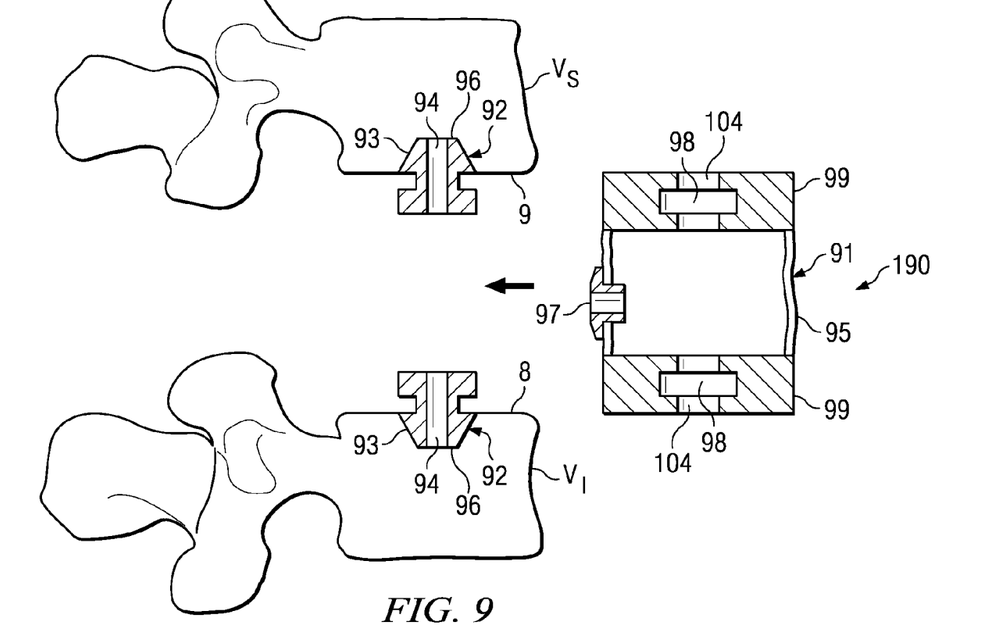
FIG. 9 is a cross-sectional view of an embodiment of an implant between vertebral bodies.

FIG. 9 illustrates an implant 190 for placement adjacent at least one vertebral endplate 8, 9. An intervertebral structure 91 is shown along with nozzles 92 having sides 93 that extend away for the intervertebral structure 91 when the implant 190 is in place between superior vertebra $V_S$ and an inferior vertebra $V_I$. The intervertebral structure 91 shown is a membrane 95 with end members 99 having slots 98 that couple with the proximal ends of the nozzles 92 when the implant 190 is fully assembled. The implant 190 is sized to replace at least a portion of a vertebral body. In FIG. 9, the implant 190 is shown prior to the intervertebral structure 91 being assembled with the nozzles 92. In some embodiments, the nozzles 92 are initially and separately attached to the superior vertebra $V_S$ and the inferior vertebra $V_I$. The end members 99 are then connected with the nozzles 92, prior to filling of the membrane 95. In other embodiments, a partially assembled or fully assembled implant 190 may be attached to the superior vertebra $V_S$ and the inferior vertebra $V_I$ prior to complete filling of the membrane 95. The illustrated sides 93 form a round cross-section. The sides 93 may also include threads, teeth, or other projections to assist with secure attachment between the nozzles 92 and respective vertebral endplates 8, 9. The nozzles 92 have a generally wider structure at their proximal ends where they couple with the intervertebral structure 91 and a more narrow structure at their distal ends 96. This shape may be useful to assist with insertion into a vertebral endplate in some embodiments, and may assist with penetration of the vertebral endplate. The nozzles 92 have openings 94 near the distal ends 96 of the sides 93. The openings 94 are configured to open through at least one vertebral endplate 8, 9 in some embodiments. When the implant 190 is assembled, the opening 94 align with end member openings 104 to allow for passage of material from within the membrane 95 into the vertebral bodies. The nozzles 92 may be sharpened or tapered overall to assist with insertion or penetration of the vertebral endplate, and it may have a sharpened distal end 96, as shown in FIG. 9, to assist with insertion or penetration of the vertebral endplate. FIG. 9 further illustrates a port 97 in the intervertebral structure 91 that is in fluid communication with the nozzles 92. In some embodiments, the port 97 is configured to receive fill material 1000.

Figure 10:
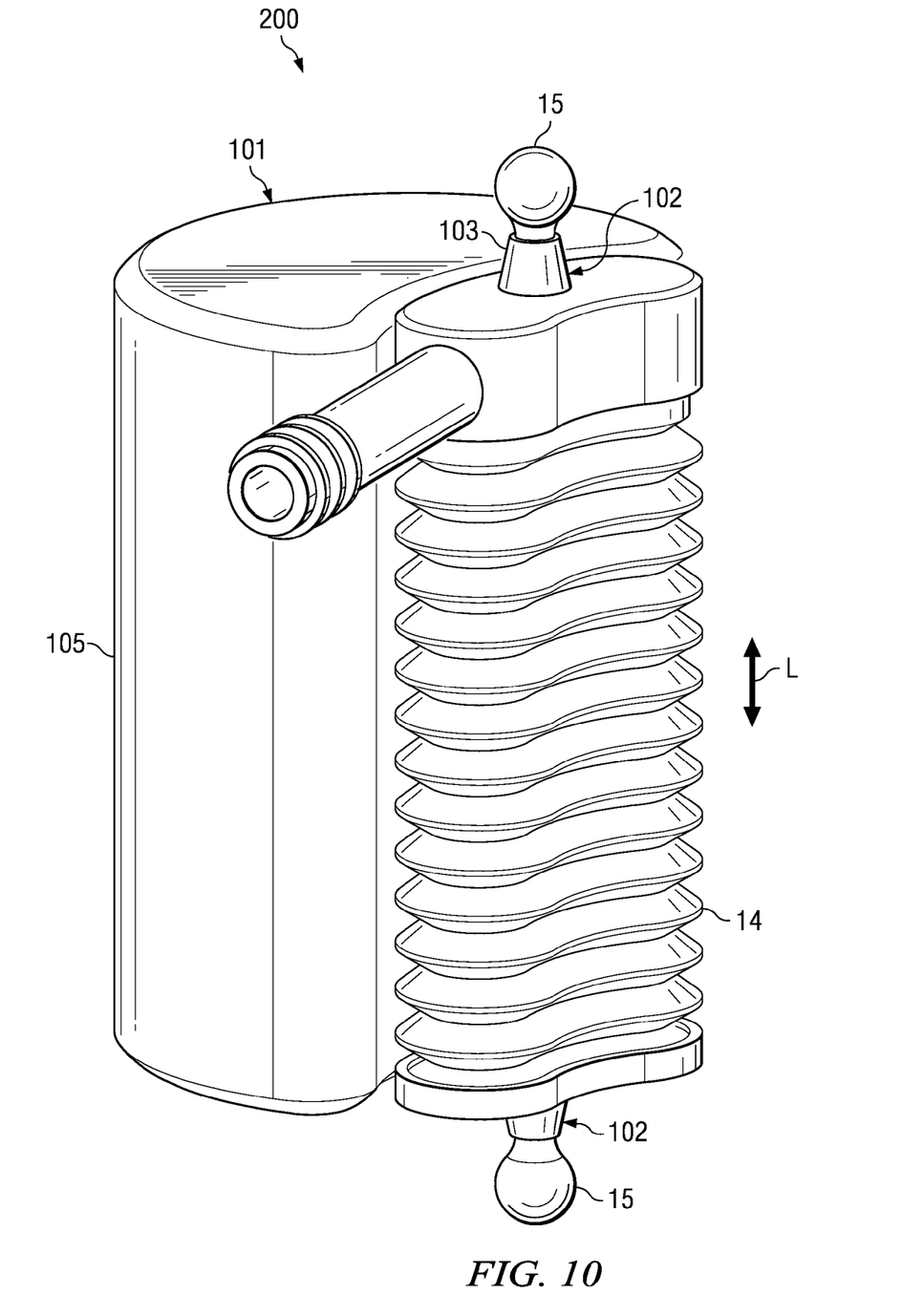
FIG. 10 is a perspective view of an embodiment of an implant.

FIG. 10 shows an implant 200 for placement adjacent at least one vertebral endplate. An intervertebral structure 101 is shown along with nozzles 102 having sides 103 that extend away for the intervertebral structure 101. The intervertebral structure 101 shown is an expandable body in an expanded state. The illustrated intervertebral structure 101 includes a laterally rigid component 14 and a membrane 105. The illustrated laterally rigid component 14 is a bellows. The longitudinal axis, or linear expansion direction L, of the laterally rigid component 3 is illustrated. Expansion of the laterally rigid component 14 may be realized by introduction of a fluid into the laterally rigid component 14, may result from elasticity in the material from which the component is made, from internal or external biasing devices, or from any other effective device for generating expansion. The cross-sectional shape of the embodiment of the laterally rigid component 14 is concave-convex. However, in other embodiments, the cross-sectional shape of the laterally rigid component 14 may be any functional shape, such as but not limited to, generally round, oval, rectangular, triangular, polygonal, or combinations of these shapes. The illustrated nozzles 102 are open to the interior of the laterally rigid component 14. A bag 15 is shown extending from an open, distal end of the nozzle 102.

The bag 15 shown is in fluid communication with the interior of the laterally rigid component 14. The nozzles 102 and bag 15 of some embodiments are configured to extend from the laterally rigid component 14 and into an endplate of an adjacent vertebra. The bag 15 may be filled with a material, such as a flowable material, to assist in attachment of the lateral rigid component 14 to the adjacent vertebra. The bag 15 may additional have a therapeutic effect on the vertebra. For example, and without limitation, the bag 15, alone or in combination with the nozzle 102, may help to stabilize the vertebra. The material used to inflate the bag 15 may be a curable material or may be a material that is used to expand the bag 15, but does not cure in place. Once expanded, the bag 15 may also receive additional materials that permanently fill the bag 15, or that have an additional therapeutic effect on the vertebra. The therapeutic effect may result from the application of a chemical or pharmaceutical effect or from a physical or thermal property, among other effects. Any of the materials for use in the bag 15 may also be a fill material 1000 as described in detail below. In addition to the nozzle 102 or bag 15, an end of an embodiment of the laterally rigid component 14 may include teeth, spikes, ridges, indentations, roughening, knurling, or any other device for enhancing fixation between a vertebra and the laterally rigid component 15.

The membrane 105 is shown in an expanded state in FIG. 10. The membrane 105 defines a volume and is shown coupled laterally adjacent to the laterally rigid component 14. The illustrated membrane 105 and the laterally rigid component 14 are adjacent, with the volume defined by the membrane 105 exclusive of the laterally rigid component 14, as defined herein. In some embodiments, it is advantageous for the membrane 105 and the laterally rigid component 14 to be configured in different volumes such that expansion of the respective devices may be controlled independently or enacted sequentially or in parallel. The membrane 105 of some embodiments is configured to be placed between vertebrae and expanded to contact the vertebrae and provide support between them. Lateral expansion of the membrane 105 is also accomplished in some embodiments. For example, in FIG. 10, anterior expansion, as well as medial-lateral expansion, and intervening radial expansions, are illustrated. As used herein, the term lateral means directions approximately normal to the linear expansion direction L.

One or both of the membrane 105 and the bag 15 may be constructed, in whole or in part, of a non-permeable material. The membrane 105 and bag 15 may include compliant or non-compliant balloon materials such as those commonly used to manufacture coronary and Kyphoplasty medical devices. Such materials may include, but not be limited to, mylar, rubber, polyurethane, vinyl, latex, polyethylenes, ionomer, and polytetrapthalate (PET), as well as less flexible materials such as Kevlar®, PEBAX®, stainless steel, titanium, nickel-titanium alloys, and other metals and alloys and/or ceramics. A compliant membrane or bag may include reinforcing to limit one or both of the size and shape of the membrane to a clinically advantageous extent. A non-compliant membrane or bag may expand more elastically to more completely fill an irregular opening, depending on the amount of material introduced into the membrane or bag.

Likewise one or both of the membrane 105 and the bag 15 may be constructed, in whole or in part, of a permeable material, which allows a certain amount of fill material 1000 to pass through the membrane 105 and bag 15. All or a portion may be made permeable by fabricating a material, including but not limited to the membrane materials listed above, into a fabric, weave, mesh, composite, bonded fiber assembly, or any other manufacture known to those skilled in the art.

The bags 15 shown in FIG. 10 are configured to receive fill material 1000 and expand through respective nozzles 102. A bag 15 may be constrained to a predetermined size, shape, or both. In some embodiments, the bag 15 is configured to be expanded to a shape that is wider in a vertebral body than an opening in a vertebral endplate through which the bag 15 was introduced.

Figure 11:
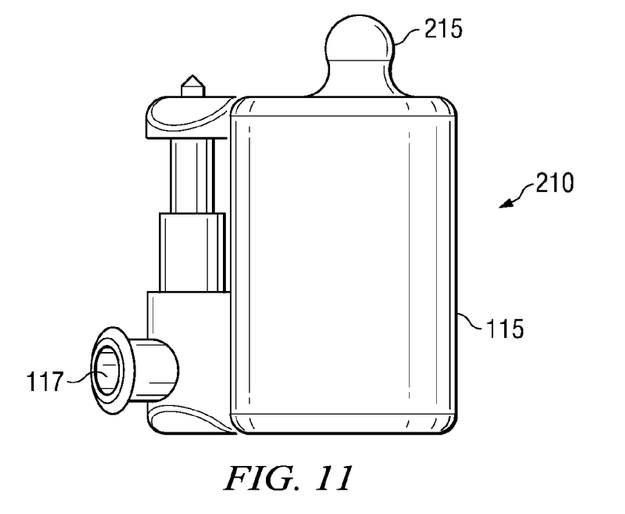
FIG. 11 is a perspective view of an embodiment of an implant.

FIG. 11 shows an embodiment with an implant 210 for placement adjacent to at least one vertebral endplate. The implant 210 is shown in an expanded state. The implant 210 of some embodiments has an intervertebral structure including a bag 215 that is next to the at least one vertebral endplate in an unexpanded state and is configured to at least in part penetrate the vertebral endplate through an aperture in the vertebral endplate in an expanded state. In some embodiments, the bag 215 is configured to expand to a greater lateral dimension inside a vertebra than the lateral dimension of the aperture in the vertebral endplate. Similar to the bag 15, the bag 215 may be constrained or unconstrained, permeable or impermeable, and any other functional shape, size, or material. A membrane 115 that is configured to expand laterally in a space between vertebrae when the implant 210 is an expanded state is also illustrated in FIG. 11. The membrane 115 may be integrated with the bag 215 and the components may share structural components in some embodiments. Alternatively, in some embodiments, the bag 215 is coupled directly to a portion of the implant 210 other than the bag 215. In some embodiments, the bag 215 and the membrane 115 are in fluid communication with a fill material 1000 source. For example and without limitation, a port 117 of the illustrated embodiment may accept a fill material 1000 that expands the telescoping portion of the implant 210 and simultaneously or in succession transfers fill material 1000 to the membrane 115 and into the bag 215.

Figure 12:
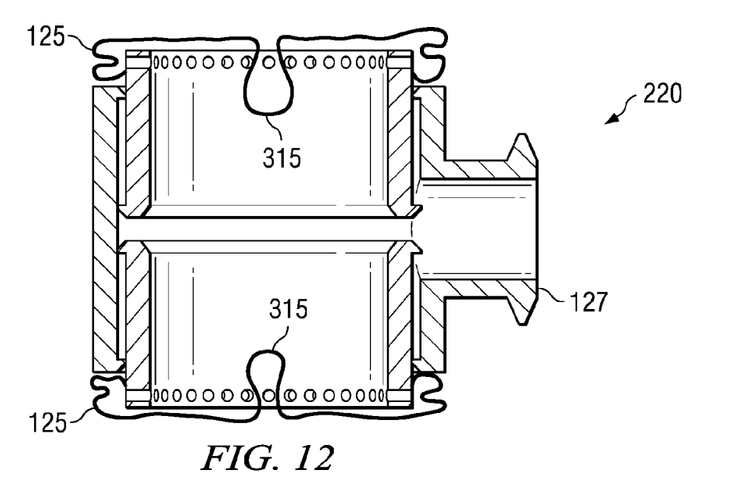
FIG. 12 is a cross-sectional view of an embodiment of an implant in an unexpanded state.
Figure 13:
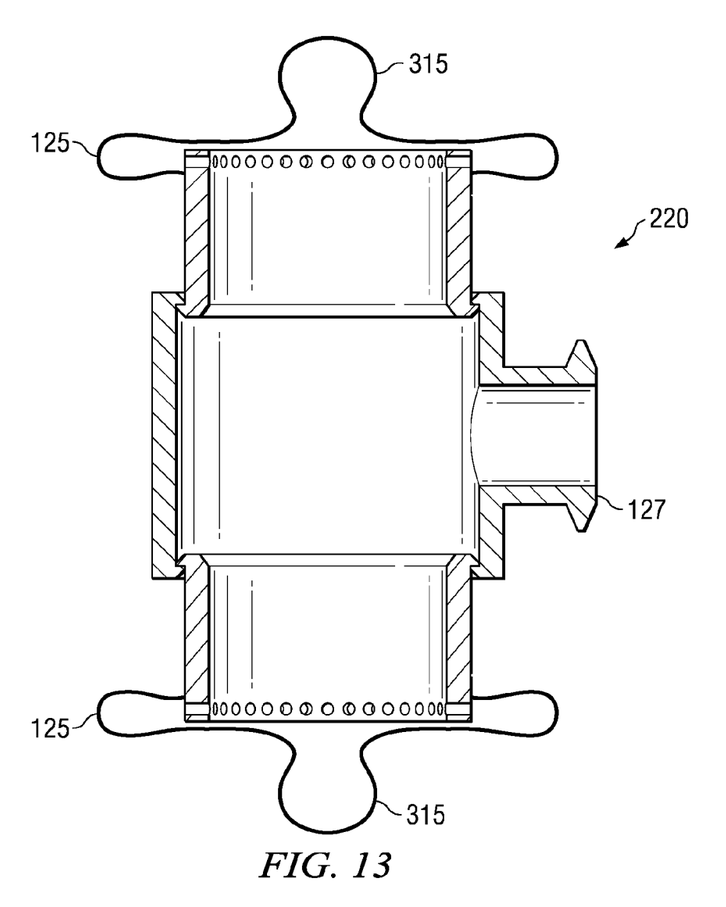
FIG. 13 is a cross-sectional view of the implant of FIG. 12 in an expanded state.

FIGS. 12 and 13 show an implant 220 for placement adjacent to at least one vertebral endplate. The implant 220 is shown in an unexpanded state in FIG. 12 and an expanded state in FIG. 13. The implant 220 of some embodiments has an intervertebral structure including a bag 315 that is next to the at least one vertebral endplate in an unexpanded state and is configured to at least in part penetrate the vertebral endplate through an aperture in the vertebral endplate in an expanded state. In some embodiments, the bag 315 is configured to expand to a greater lateral dimension inside a vertebra than the lateral dimension of the aperture in the vertebral endplate. Similar to the bag 15, the bag 315 may be constrained or unconstrained, permeable or impermeable, and any other functional shape, size, or material. A membrane 125 that is configured to expand laterally in a space between vertebrae when the implant 220 is an expanded state is also illustrated in FIGS. 12 and 13. The membrane 125 may be integrated with the bag 315 and the components may share structural components in some embodiments. Alternatively, in some embodiments, the bag 315 is coupled directly to a portion of the implant 220 other than the bag 315. In some embodiments, the bag 315 and the membrane 125 are in fluid communication with a fill material 1000 source. For example and without limitation, a port 127 of the illustrated embodiment may accept a fill material 1000 that expands the telescoping portion of the implant 220 and simultaneously or in succession transfers fill material 1000 to the membrane 125 and into the bag 315.

Figure 14:
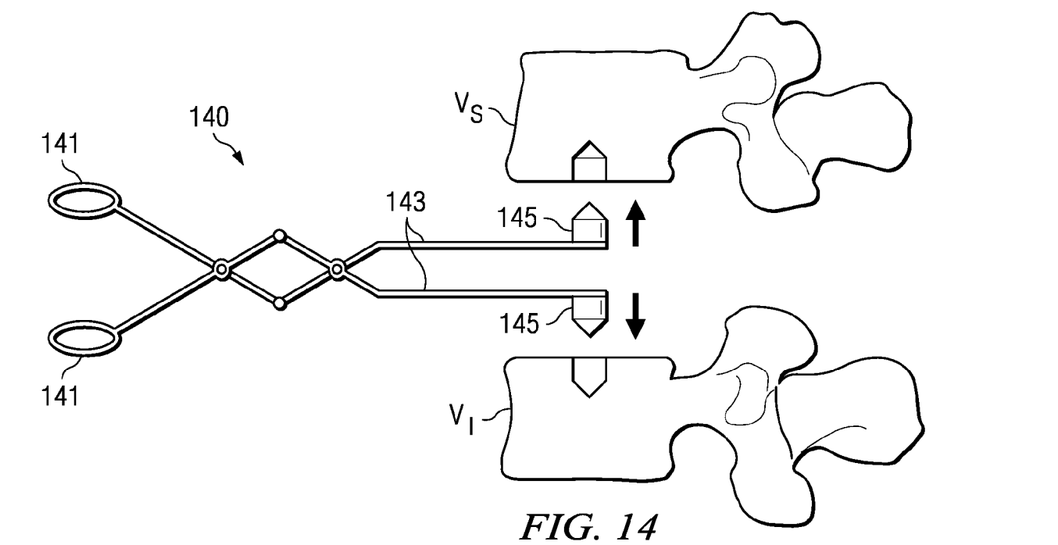
FIG. 14 is a cross-sectional view of vertebrae that have been acted on by the illustrated preparatory instrument.

FIG. 14 illustrates preparation of a superior vertebra $V_S$ and an inferior vertebra $V_I$ with a punch 140 instrument. The illustrated preparation may be associated with certain embodiments of the invention where it is desirable to form an aperture in or through a vertebral endplate. The punch 140 has handles 141 and linkages 143 configured such that force applied to the handles 141 is transferred through the linkages 143 to push tips 145 into the superior vertebra $V_S$ and the inferior vertebra $V_I$, respectively, to form apertures in or through the endplates of the vertebrae. The applied force results in movement of the push tips 145 in the direction of the arrows shown. In another embodiment, a punch instrument may include one push tip 145 and an opposite tip that provides a surface against which to push. In such an embodiment, the instrument may be used first to create an opening in one of the superior vertebra $V_S$ and the inferior vertebra $V_I$, and then the instrument could be flipped to create an opening in the other vertebra.

Figure 15:
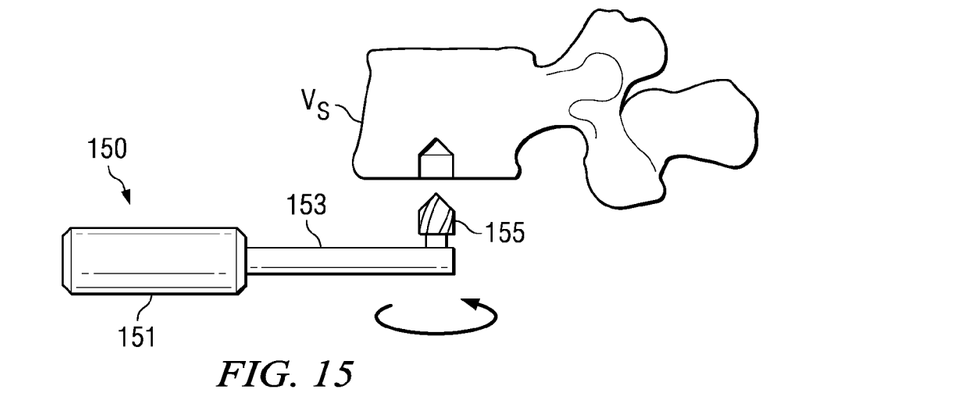
FIG. 15 is a cross-sectional view of a vertebra that has been acted on by the illustrated preparatory instrument.

FIG. 15 shows another instrument that may be used to form an aperture in or through a vertebral endplate, such as a superior vertebra $V_S$. The instrument shown is an angle drill 150. The angle drill 150 illustrated has a motor 151, a shaft 153 coupled to the motor 151, and a bit 155 coupled to the shaft 153. The illustrated angle drill 150 forms a right angle between the shaft 153 and the bit 155. However, other embodiments may have a bit at any angle between 0 degrees and 180 degrees. Various angulations may be advantageous to avoid sensitive anatomical structures from various surgical approaches. The motor 151 of some embodiments turns all or part of the shaft 153, which in turn transfers the rotational motion along the shaft 153 through an angle to turn the bit 155. The illustrated bit 155 has a sharpened tip, but may also have a square tip or any other functional shape. The angle drill 150 may be rotated 90 degrees about the shaft 153 and directed to form an aperture in or through an endplate of an inferior vertebra $V_I$.

Figure 16:
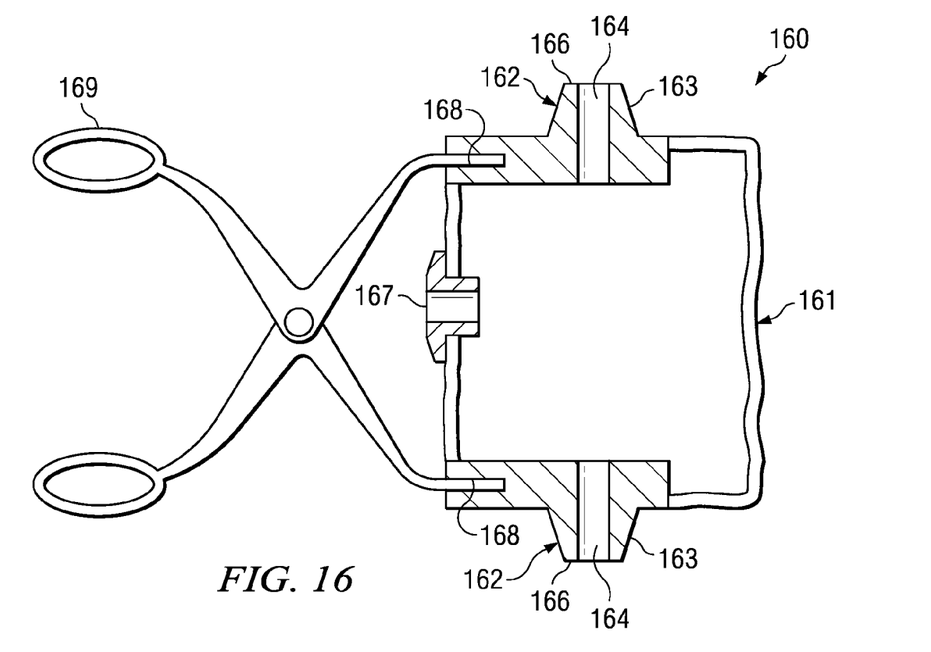
FIG. 16 is a cross-sectional view of an embodiment of an implant in combination with a preparatory instrument.

FIG. 16 shows an implant 160 for placement adjacent at least one vertebral endplate. An intervertebral structure 161 is shown along with a nozzle 162 having sides 163 that extend away for the intervertebral structure 161. The intervertebral structure 161 shown is a vertebral body replacement device sized to replace at least a portion of a vertebral body. The intervertebral structure 161 includes a membrane 165 and is shown in fluid communication with the nozzles 162 through the intervertebral structure 161, and specifically through the membrane 165 that couples with the nozzles 162 and a port 167. The port 167 may be used to receive a fill material 1000 into the implant 160. The illustrated sides 163 shown form a round cross-section. The nozzles 162 have openings 164 near distal ends 166 of the sides 163. The openings 164 are configured to open through at least one vertebral endplate in some embodiments. The nozzles 162 may be sharpened or tapered overall to assist with insertion or penetration of the vertebral endplate, and it may have a sharpened distal end 166 to assist with insertion or penetration of the vertebral endplate. The intervertebral structure additionally includes connection holes 168 to receive a spreader instrument 169. The connection holes 168 may be of any functional configuration such as, but not limited to, round, oval, rectangular, slotted, threaded, or notched. The spreader instrument 169 may also be of any functional configuration capable of at least one of spreading, holding expansion, or contracting the intervertebral structure 161. Another embodiment of a spreader instrument includes separate sticks, rods, or other longitudinal instruments that may be separately placed in the connection holes 168 and used to move the intervertebral structure 161.

Figure 17:
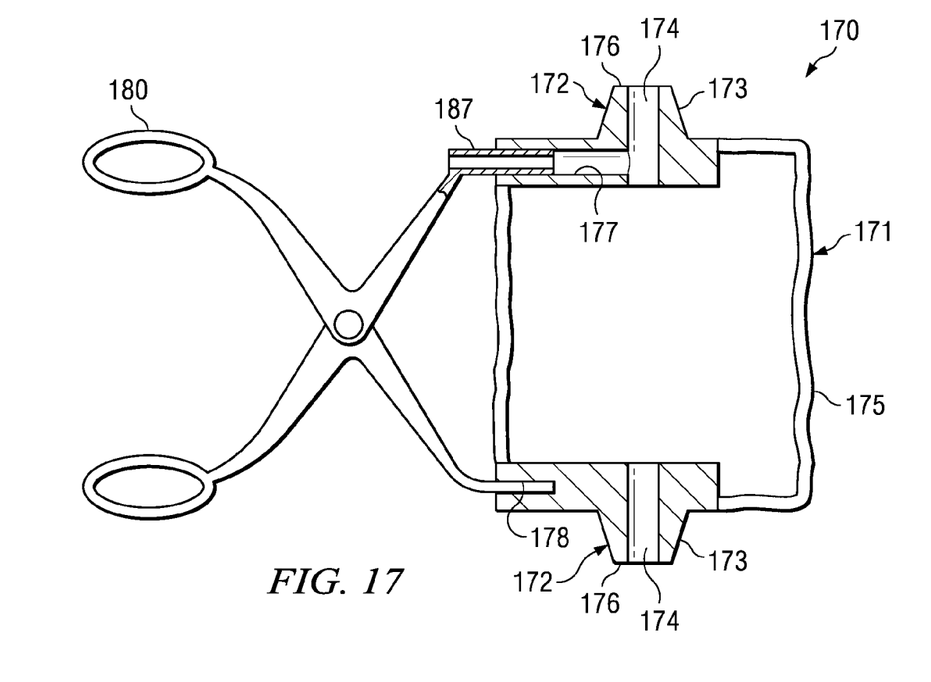
FIG. 17 is a cross-sectional view of an embodiment of an implant in combination with a preparatory instrument.

FIG. 17 illustrates an implant 170 for placement adjacent at least one vertebral endplate. An intervertebral structure 171 is shown along with a nozzle 172 having sides 173 that extend away for the intervertebral structure 171. The intervertebral structure 171 shown is a vertebral body replacement device sized to replace at least a portion of a vertebral body. The intervertebral structure 171 includes a membrane 175 and is shown in fluid communication with the nozzles 172 through the intervertebral structure 171, and specifically through the membrane 175 that couples with the nozzles 172 and a port 177. The port 177 may be used to receive a fill material 1000 into the implant 170. The illustrated sides 173 shown form a round cross-section. The nozzles 172 have openings 174 near distal ends 176 of the sides 173. The openings 174 are configured to open through at least one vertebral endplate in some embodiments. The nozzles 172 may be sharpened or tapered overall to assist with insertion or penetration of the vertebral endplate, and it may have a sharpened distal end 176 to assist with insertion or penetration of the vertebral endplate. The intervertebral structure 171 additionally includes a connection hole 178 and the port 177 to receive a spreader instrument 180. As noted above, the port 177 may be used to receive a fill material 1000 in addition to its function of receiving a portion of the spreader instrument 180. As illustrated, the portion of the spreader instrument 180 that connects with the port 177 is a connection cannula 187. A fill material source may be attached to the connection cannula 187 to pass fill material 1000 into the port 177 and into the membrane 175 and the openings 174. The connection hole 178 and the port 177 may be of any functional configuration such as, but not limited to, round, oval, rectangular, slotted, threaded, or notched. The spreader instrument 180 may also be of any functional configuration capable of at least one of spreading, holding expansion, or contracting the intervertebral structure 171. In similar embodiments, a valve, a series of valves, or configurations of conduits may be used to simultaneously or selectively pass fill material 1000 through or into one or all of the openings 174 and the membrane 175. Valves used with any embodiment may be pressure activated valves that pass material without further user intervention once a threshold pressure is reached.

A method embodiment is a method of stabilizing a spine that includes forming an aperture in a vertebral endplate. FIGS. 14 and 15 depict examples of instruments that are suited for forming apertures in vertebral endplates. Additionally, a nozzle of an embodiment of the invention may be pressed against or even through a vertebral endplate to form an aperture. As described in greater detail above, any of the nozzle embodiments may be sharpened, shaped, or include sharpened or shaped components that assist with the penetration of a vertebral endplate. The method embodiment may further include placing an implant with a bag (15, 215, 315) in an unexpanded state adjacent to the vertebral endplate aperture. A fill material may be introduced into the bag to expand the bag through the vertebral endplate aperture and into a vertebra. Introducing the fill material in some embodiments may laterally expand the bag to a lateral dimension that is greater than a lateral dimension of the aperture in the vertebral endplate. The expanded bag of some embodiments would then be difficult to move back through the aperture and thereby more positively fix the implant to the vertebra. The expanded bag may also treat the vertebra to which it is attached by applying treatment such as, but not limited to, the treatment associated with Kyphoplasty or vertebroplasty. For example and without limitation, a bag, alone or in combination with a nozzle, provide stabilization to a vertebra. The material used to inflate the bag may be a curable material or may be a material that is used to expand the bag, but does not cure in place. This material may have a therapeutic effect on the vertebra. Once expanded, the bag may also receive additional materials that permanently fill the bag, or that have an additional therapeutic effect on the vertebra. The therapeutic effects may result from the application of a chemical or pharmaceutical effect or from a physical or thermal property, among other effects.

In some embodiments, such as the device of FIG. 17, the act of introducing fill material includes introducing fill material through an instrument used to position the implant relative to the vertebral endplate. The spreader instrument 180 has a connection cannula 187 through which such an act may be accomplished.

The embodiments of FIGS. 16 and 17 show examples of surgical instruments that may be used to hold an implant adjacent to a vertebral endplate while a fill material is introduced into the bag. In other embodiments, such a surgical instrument may be a mechanism internal to the implant that is controlled remotely by a user of the implant. Such a mechanism may be a wire, string, release or other control effective to transmit a force or signal to the implant.

The fill material 1000 may enter an implant as a fluid, and then harden or cure in the implant. In some embodiments, a non-hardenable and non-curing fluid is used to expand, or to hold expansion in the implant or one or some of the components of the implant. A fill material 1000 may then be introduced into the implant. The fill material 1000 may be a paste, gel, liquid, suspension, granular mixture, or similar substance. Non-limiting examples of fill materials 1000 include bone cement, paste, morselized allograft, autograft, or xenograft bone, ceramics, or various polymers. An example bone cement is polymethylmethacrylate (PMMA), which may be made from methylmethacrylate, polymethylmethacrylate, esters of methacrylic acid, or copolymers containing polymethylmethacrylate and polystyrene. Additional non-limiting examples of the fill material 1000 include semi-rigid flowable or hardenable material such as silicone or various types of urethane materials. It should further be understood that other types of fill materials 1000 which are not necessarily hardenable or curable may be used in association with the present invention. For example, the fill material may comprise beads or small particles or grains of material, some of which may, in aggregate, achieve a harder consistency as a result of interlocking or compaction. In some embodiments, the fill material may also include a bone growth promoting substance.

For embodiments of each of the implants disclosed herein, the size or shape of the membrane may be limited to only fill a particular portion of a vertebral space. For example, and without limitation, an implant may be configured to only occupy a lateral portion of a vertebral space to accomplish a hemi-vertebrectomy. Implants may be alternatively shaped to occupy other, limited portions of a vertebral space.

Embodiments of the implant in whole or in part may be constructed of biocompatible materials of various types. Examples of implant materials include, but are not limited to, non-reinforced polymers, carbon-reinforced polymer composites, PEEK and PEEK composites, low density polyethylene, shape-memory alloys, titanium, titanium alloys, cobalt chrome alloys, stainless steel, ceramics and combinations thereof. If a trial instrument or implant is made from radiolucent material, radiographic markers can be located on the trial instrument or implant to provide the ability to monitor and determine radiographically or fluoroscopically the location of the body in the spinal space. In some embodiments, the implant or individual components of the implant may be constructed of solid sections of bone or other tissues. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof.

Embodiments of the invention may be applied to one or all of the lumbar spinal region, the cervical spinal region, and the thoracic spinal region, or between other skeletal structures. Some embodiments may also include supplemental fixation devices in addition to or as part of the expandable medical implant for further stabilizing the anatomy. For example, and without limitation, rod and screw fixation systems, anterior, posterior, or lateral plating systems, facet stabilization systems, spinal process stabilization systems, and any devices that supplement stabilization may be used as a part of or in combination with the expandable medical implant.

Implant embodiments of the invention may preferably be implanted from a generally posterior approach. However, embodiments of the invention may include implantation from any surgical approach, including but not limited to, posterior, lateral, anterior, transpedicular, lateral extracavitary, in conjunction with a laminectomy, in conjunction with a costo-transversectomy, or by any combination of these and other approaches.

Various method embodiments of the invention are described herein with reference to particular expandable medical implants. However, in some circumstances, each disclosed method embodiment may be applicable to each of the expandable medical implants, or to some other implant operable as disclosed with regard to the various method embodiments.

Terms such as lower, upper, anterior, posterior, inferior, superior, lateral, medial, contralateral, and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An implant for placement adjacent to at least one vertebral endplate comprising:
    an intervertebral structure with an exterior wall that encloses a hollow interior;
    a nozzle that extends through the exterior wall and includes a base recessed within the hollow interior and an outwardly-extending tapered section that extends away from the base to penetrate the vertebral endplate, the tapered section includes a wider proximal end at the base and a narrower distal end away from the base, the nozzle further including at least one bore that extends through the base and the tapered section and is in communication with the hollow interior of the intervertebral structure;
    the base being wider than the tapered section measured in a direction across the bore, and the base having a greater thickness than the exterior wall; and
    a port that extends through the exterior wall in the intervertebral structure and is in fluid communication with the nozzle, the port being spaced away from the nozzle.

2. The implant of claim 1, wherein the nozzle is sharpened to assist with insertion or penetration of the vertebral endplate.

3. The implant of claim 1, further comprising a seal between the nozzle and the vertebral endplate.

4. The implant of claim 1, further comprising a fill material to be forced through the nozzle.

5. The implant of claim 1 wherein an outer surface of the base is flush with an outer surface of the exterior wall.

6. The implant of claim 1 further comprising a ring seal that extends around an exterior of the nozzle at an intersection between the base and the tapered section.

7. The implant of claim 1 further comprising a plurality of projections that extend laterally outward from the tapered section and angle downward towards the base.

* * * * *